United States Patent [19]

Crump et al.

[11] Patent Number: 4,472,200
[45] Date of Patent: Sep. 18, 1984

[54] NEW ADDITIVES FOR RETARDING SETTING OF CEMENT FROM METHYLENEPHOSPHONATED AMINOHYDROCARBYLPIPERAZINE-UREA ADDUCTS

[75] Inventors: Druce K. Crump, Lake Jackson; David A. Wilson, Richwood, both of Tex.

[73] Assignee: The Dow Chemical Company, Midland, Mich.

[21] Appl. No.: 528,831

[22] Filed: Sep. 2, 1983

[51] Int. Cl.$^3$ .............................................. C04B 7/35
[52] U.S. Cl. ........................................ 106/90; 106/315
[58] Field of Search ................................... 106/90, 315

[56] References Cited

U.S. PATENT DOCUMENTS

| | | | |
|---|---|---|---|
| 3,346,487 | 10/1967 | Iraul et al. | 252/8.5 |
| 3,346,488 | 10/1967 | Lyons et al. | 252/8.5 |
| 3,409,080 | 11/1968 | Harrison | 166/31 |
| 3,654,151 | 4/1972 | King et al. | 252/8.5 C |
| 3,657,134 | 4/1972 | King et al. | 252/8.5 C |
| 3,794,506 | 2/1974 | Schmidt et al. | 106/90 |
| 3,865,803 | 2/1975 | Falkehag | 260/124 A |
| 3,964,921 | 6/1976 | Persinski et al. | 106/90 |
| 4,040,854 | 8/1977 | Persinski et al. | 106/90 |
| 4,066,469 | 1/1978 | Shiel et al. | 106/89 |
| 4,225,361 | 9/1980 | Joseph | 106/111 |
| 4,401,473 | 8/1983 | Kleiner et al. | 106/109 |

OTHER PUBLICATIONS

Chem. Abstracts: 97, 112352a-"Plugging Composition for Cementing Oil and Gas Wells", Dytyuk, L. T. et al.
Chem. Abstracts: 97, 26178a-"Plugging Fluids for Cementing Deep Petroleum and Gas Wells", Alekseev, P. D., et al.
Chem. Abstracts: 98, 58912p-"Improvement of Casing Cementation in Deep and Ultradeep Wells, Part 2, Deep Well Cements and Additives", Arens, K. H. et al.
SU-640-019, "Plugging Mixture for High-Temperature Oil or Gas Wells-Comprises Portland Cement and 1-Hydroxy Ethylidene-Phosphonic Acid Sodium or Potassium Salt", Khariv I YU.
"Additives Tailor Cement to Individual Wells", P. N. Parker, C. Clement, *The Oil and Gas Journal*, Mar. 14, 1977, vol. 75.

*Primary Examiner*—James Poer
*Attorney, Agent, or Firm*—A. C. Ancona

[57] ABSTRACT

Certain methylenephosphonic acid derivatives of aminohydrocarbylpiperazine-urea adducts have been found to be good cement set-retarding additives.

16 Claims, No Drawings

NEW ADDITIVES FOR RETARDING SETTING OF CEMENT FROM METHYLENEPHOSPHONATED AMINOHYDROCARBYLPIPERAZINE-UREA ADDUCTS

BACKGROUND OF THE INVENTION

Hydrophobic-substituted phosphonic or phosphinic acids and their alkali metal salts have been used in cements, primarily soil/cement mixtures, to improve the freeze-thaw properties and salt-resistance. Six- to eighteen-carbon alkyl phosphonic acids or their alkali metal salts are so described in U.S. Pat. No. 3,794,506. A plugging mixture for high temperature oil and gas wells comprising Portland cement and 1-hydroxy ethylidenephosphonic acid trisodium or tripotassium salts as set time extenders is described in Derwent abstract 71376B/39 (1979) of USSR Pat. No. 640,019. The use of these phosphonate salts at temperatures of 75° to 150° C. in amounts of 0.1-0.3% by weight is described in the abstract.

Other organic phosphorous acid derivatives are taught to be useful additives in cement compositions as turbulence-inducing and flow-property improver additives (U.S. Pat. Nos. 3,964,921 and 4,040,854, respectively). Another turbulence-inducer is a pyrolysis product of urea and a bis(alkylenepyrophosphate) (U.S. Pat. No. 3,409,080).

Alkylene diphosphonic acids and their water soluble salts are described as set time extenders and water reducing agents for gypsum plasters (U.S. Pat. No. 4,225,361). Lignins which have been phosphonoalkylated through an ether linkage or corresponding sulfonates, sulfides, hydroxyl or amine derivatives are taught to be useful primarily as dispersants or surfactants (U.S. Pat. No. 3,865,803) and are also said to be useful as "cement additives" without indicating specific uses.

Ultra-rapid hardening Portland cement compositions are described which contain various acid salt additives (U.S. Pat. No. 4,066,469). It states that use of acid phosphates as the acid salt additives is excluded since the phosphates have a characteristically powerful retarding property peculiar to them.

Most of the cement used in oil wells is called portland cement. Portland cement is manufactured by calcining raw materials consisting of limestone, clay, shale, and slag together at 2,600° to 2,800° F. in a rotary kiln.

The resulting material, is cooled and interground with small percentages of gypsum to form portland cement. In addition to the above raw materials, other components such as sand, bauxite, iron oxide, etc., may be added to adjust the chemical composition depending upon the type of portland cement desired.

The principal components of the finished portland cement are lime, silica, alumina, and iron. These components form the following complex compounds: Tricalcium aluminate, (3CaO.Al$_2$O$_3$), tetracalcium aluminoferrite, (4CaO.Al$_2$O$_3$.Fe$_2$O$_3$), tricalcium silicate, (3CaO.SiO$_2$), and dicalcium silicate, (2CaO.SiO$_2$).

When water is added to cement, setting and hardening reactions begin immediately. The chemical compounds in the cement undergo the processes of hydration and recrystallization which results in a set product. The maximum amount of water that can be used with an oil-well cement is the amount which can be added before solids separation occurs. The minimum amount of water is the amount required to make the slurry pumpable. Therefore, the normal water ratio is governed by the maximum and minimum limits for a particular class of cement.

Thickening time is the time that the cement remains pumpable in the well. This is the most critical property of an oil-well cement. The thickening time has to be long enough to be pumped into place and short enough to permit operations to resume quickly. Generally, 3 hours provides the necessary placement time plus a safety factor.

Other factors, such as fluid loss, viscosity and density must be taken into consideration and additives are known to the art-skilled which affect each of these factors as well as that of set, or thickening, time as mentioned above. Another parameter which has an effect on set time is temperature. Cement sets more rapidly as the temperature increases. This must be taken into consideration particularly when pumping cement into deeper wells since temperature increases as the depth of the well becomes greater. Temperature also affects the strength of the cement, the strength becoming less as the temperature increases.

Because of this temperature effect, it is important to retard the setting of the cement employed in the deeper wells.

It has now been discovered that certain new phosphonomethylated compounds are useful in aqueous cement slurries as set retarding additives. Some of these compounds are chelating agents, while others are useful as threshold agents in retarding the precipitation of metal ions from aqueous solution. However, not all such compounds are useful as cement set-retarders.

The compounds and their preparation, herein disclosed as useful, have been disclosed in our copending application Ser. No. 528,835 filed concurrently herewith, entitled "New Methylene Phosphonic Acid Inhibitor Compositions Derived from Aminohydrocarbylpiperazine-Urea Adducts".

SUMMARY OF THE INVENTION

The cement set-retarding compounds of the present invention are compounds having the formula:

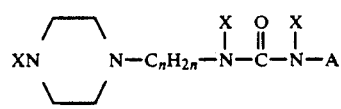

wherein A is

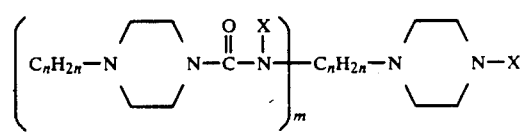

wherein X is

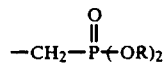

or H, and wherein R is H, ammonium, an alkali or alkaline earth metal, m is 0-2, n is 2 or 3 and wherein at least one X is

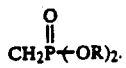

DETAILED DESCRIPTION OF THE INVENTION

The following examples show typical preparations of the compounds useful for retarding the setting of cement.

EXAMPLE 1

One hundred fifty gm (0.53 mole) of an aminoethylpiperazine/urea (2/1 mole ratio) reaction product and 90 gm of deionized water were added to a 500 ml round-bottom reaction flask equipped with a water-cooled reflux condenser, mechanical stirrer, thermometer with a temperature controller, and an addition funnel. Approximately 200 gm of concentrated hydrochloric acid and 92 gm (1.1 moles) of phosphorous acid were added with stirring and the mixture heated to reflux and maintained for one hour. Paraformaldehyde (37 g, 91%, 1.1 moles) was added over a one-hour period. The reaction mixture was heated at reflux for an additional two hours and then cooled. The product was evaluated as a cement set retarder. Results are shown in Table I.

EXAMPLE 2

The aminoethylpiperazine/urea product of Example 1 was phosphonomethylated with approximately 4 mole equivalents of formaldehyde and phosphorous acid according to the general procedure of Example 1. The product was evaluated as a cement set retarder.

EXAMPLE 3

An aminoethylpiperazine/urea reaction product (1/1 mole ratio) was phosphonomethylated using the general procedure of Example 1. The reaction product was evaluated as a cement retarder.

The following test was used in determining whether a given compound was useful as a set retarding agent:
1. The following ingredients were weighed:
   cement—100 g
   water—38 g
   additive—0.2 g active
2. Water and liquid additive were mixed;
3. Cement was added to liquid, the bottle tightly closed and shaken to mix;
4. Bottle was placed in a pre-heated 180° F. bath;
5. Setting of cement was checked after 6 and 24 hours.

A blank (no additive) was run for comparison with each of the additives. The test was run at 180° F. (82.2° C.).

TABLE I

| | Cement Modification Data | |
| --- | --- | --- |
| | Time of Observation | |
| Additive | 6 Hrs. | 24 Hrs. |
| Example 1 | retarding - not set, dispersing | retarding - not set, dispersing |
| Example 2 | retarding - not set, dispersing | retarding - not set, dispersing |
| Example 3 | retarding - not set, dispersing | retarding - not set, dispersing |
| None (blank) | set by 6 hrs. | — |

EXAMPLE 4

The product of Example 2 above was tested as a cement retarder according to Section 8, API Specification 10, using a base slurry, a class H oilfield cement, 50% by weight water, 35% by weight silica flour, based on weight cement employed. The test was run at 400° F. (204.4° C.) to determine thickening time. Thickness of 70 Bc (Bearden consistency unit) was determined vs. time. Different amounts of the retarder (based on weight of cement) were used. With 0.2, 0.5 and 0.7 percent of the retarder thickening time was 60, 180 and 300 minutes, respectively.

We claim:

1. In a process for retarding the setting of an aqueous cement slurry which comprises adding to said slurry an organic phosphonate, the improvement which comprises employing a compound of the formula

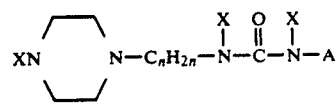

wherein A is

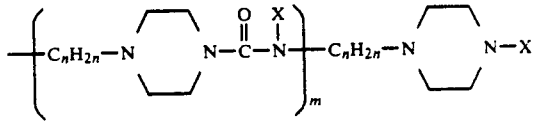

wherein X is

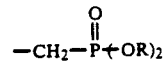

or H, and R is H, ammonium, an alkali or alkaline earth metal, m is 0–2, n is 2 or 3, and wherein at least one X is

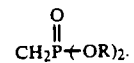

2. The process of claim 1 wherein A is

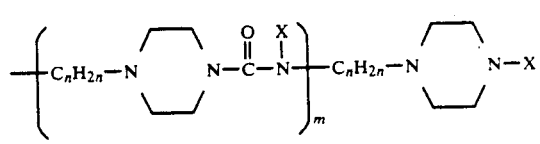

and m is 0.

3. The process of claim 1 wherein A is X.

4. The process of claim 2 wherein half the X substituents are hydrogen.

5. The process of claim 3 wherein half the X substituents are hydrogen.

6. The process of claim 1 wherein each R is an alkaline earth metal.

7. The process of claim 2 wherein each R is an alkaline earth metal.

8. The process of claim 3 wherein each R is an alkaline earth metal.

9. The process of claim 2 wherein each R is an alkali metal or ammonium.

10. The process of claim 3 wherein each R is an alkali metal or ammonium.

11. The process of claim 4 wherein the R groups are an alkaline earth metal.

12. The process of claim 5 wherein the R groups are an alkaline earth metal.

13. The process of claim 7 wherein the alkaline earth metal is calcium.

14. The process of claim 8 wherein the alkaline earth metal is calcium.

15. The process of claim 11 wherein the alkaline earth metal is calcium.

16. The process of claim 12 wherein the alkaline earth metal is calcium.

* * * * *

UNITED STATES PATENT AND TRADEMARK OFFICE
CERTIFICATE OF CORRECTION

PATENT NO. : 4,472,200
DATED : September 18, 1984
INVENTOR(S) : Druce K. Crump and David A. Wilson It is certified that error appears in the above—identified patent and that said Letters Patent is hereby corrected as shown below:

Column 2, line 55, at the end of the line after the formula add the words --or X--.

Column 4, line 30, at the end of the line after the formula add the words --or X and--.

Signed and Sealed this

Ninth Day of April 1985

[SEAL]

Attest:

DONALD J. QUIGG

Attesting Officer

Acting Commissioner of Patents and Trademarks